(12) United States Patent
Kim

(10) Patent No.: US 11,944,290 B2
(45) Date of Patent: Apr. 2, 2024

(54) TISSUE PROTECTION DEVICE FOR MITRAL VALVE MEMBRANE CERCLAGE PROCEDURE

(71) Applicant: TAU-PNU MEDICAL, Busan (KR)

(72) Inventor: June-Hong Kim, Busan (KR)

(73) Assignee: TAU-PNU MEDICAL CO., LTD., Busan (KR)

( * ) Notice: Subject to any disclaimer, the term of this patent is extended or adjusted under 35 U.S.C. 154(b) by 0 days.

(21) Appl. No.: 16/917,554

(22) Filed: Jun. 30, 2020

(65) Prior Publication Data

US 2020/0330091 A1    Oct. 22, 2020

Related U.S. Application Data

(63) Continuation of application No. 15/312,660, filed as application No. PCT/KR2015/004728 on May 12, 2015, now Pat. No. 10,729,427.

(30) Foreign Application Priority Data

May 20, 2014   (KR) ........................ 10-2014 0060587

(51) Int. Cl.
*A61B 17/04* (2006.01)
*A61B 17/00* (2006.01)
*A61B 90/00* (2016.01)
*A61F 2/24* (2006.01)

(52) U.S. Cl.
CPC .......... *A61B 17/0493* (2013.01); *A61B 17/00* (2013.01); *A61B 90/00* (2016.02); *A61B 90/04* (2016.02); *A61F 2/2451* (2013.01); *A61B 2017/00243* (2013.01); *A61B 2017/00477* (2013.01); *A61F 2/2466* (2013.01)

(58) Field of Classification Search
CPC .. A61B 17/0493; A61F 2/2451; A61F 2/2466; A61F 2/2442; A61F 2/2445; A61F 2/2448; A61F 2/2454; A61F 2/2457; A61F 2/246; A61F 2/2463

See application file for complete search history.

(56) References Cited

U.S. PATENT DOCUMENTS

| | | | | |
|---|---|---|---|---|
| 6,074,407 A | * | 6/2000 | Levine | A61B 17/1214 606/194 |
| 2003/0195563 A1 | * | 10/2003 | Foerster | A61B 17/0401 606/232 |
| 2007/0100257 A1 | * | 5/2007 | Melsheimer | A61M 25/09 606/113 |

(Continued)

*Primary Examiner* — Martin T Ton
(74) *Attorney, Agent, or Firm* — Justin Kim

(57) ABSTRACT

The present invention relates to a tissue protection device for mitral valve cerclage annuloplasty and, more particularly to a tissue protection device for protecting tissues of the body (heart) during mitral valve cerclage annuloplasty that is performed on a mitral valve cerclage patient with mitral regurgitation. The tissue protection device for mitral valve cerclage annuloplasty of the present invention is a hollow cylindrical tube where cerclage sutures (10a, 10b) are inserted, in which a hole (22) is formed at a predetermined portion of the cylindrical tube so that a coronary sinus cerclage suture (10a) inserted in a coronary sinus comes out of the cylindrical tube, and a lower section from the hole is inserted into the tricuspid valve to protect tissues of the tricuspid valve and the ventricular septum.

11 Claims, 3 Drawing Sheets

(56) References Cited

U.S. PATENT DOCUMENTS

| | | | |
|---|---|---|---|
| 2007/0185532 A1* | 8/2007 | Stone | A61B 17/0482 606/232 |
| 2008/0071364 A1* | 3/2008 | Kaye | A61F 2/2445 623/2.11 |
| 2012/0029629 A1* | 2/2012 | Kim | A61F 2/2451 623/2.11 |
| 2012/0179246 A1* | 7/2012 | Kim | A61F 2/2451 623/2.36 |

* cited by examiner

TISSUE PROTECTION DEVICE FOR MITRAL VALVE MEMBRANE CERCLAGE PROCEDURE

TECHNICAL FIELD

The present invention relates to a tissue protection device for mitral valve cerclage annuloplasty and, more particularly to a tissue protection device for protecting tissues of a body (heart) during mitral valve cerclage annuloplasty that is performed on a mitral valve cerclage patient with mitral regurgitation.

BACKGROUND ART

The heart is the center of the human circulatory system that pumps blood through our body. It is a muscle that pumps the blood only in one direction. In order for the heart to effectively maintain this unidirectional flow of blood, it must have properly functioning valves that prevent back flow through its system, or regurgitation. The heart is divided into four chambers: right and left atrium, and right and left ventricles. The four chambers are connected to the aorta, inferior and superior vena cava, pulmonary artery, and pulmonary veins.

The mitral valve (MV) separates left atrium from left ventricle while the tricuspid valve (TV) separates right atrium from the right ventricle. The aortic valve (AV) is located between the left ventricle and the aorta while the pulmonary valve (PV) is located between the right ventricle and the pulmonary artery.

Generally, valves should open and close completely with every heart beat or contraction. Incomplete opening or closing of the valves causes improper flow of blood. Valvular diseases are divided into two categories, regurgitation and stenosis. Regurgitation is a failure of a valve to close completely and stenosis is a failure of a valve to open completely.

Mitral valve regurgitation (MVR) is a common cardiac valve disorder that is caused by incomplete closure of the mitral valve (MV). The MV is located between the left atrium and the left ventricle. Over time, MVR places a burden on the heart and worsens its ability to pump blood properly. Such stress on the heart will ultimately lead to heart failure.

Traditional treatment for worsening MVR requires open heart surgery with sternotomy or thoracotomy with cardiac arrest and cardio-pulmonary bypass. Once the chest is open and access to heart is gained, the MV is either repaired or replaced using an artificial valve. Although very effective, this open-heart procedure is a high risk surgery accompanied by substantial morbidity and prolonged convalescence. Mortality due to surgery itself can be as high as 5%. As a result, the procedure often is not offered to patients who are insufficiently symptomatic to justify the surgical risk and morbidity, or to patients with substantial co-morbidity. It is reserved only for those with severe symptomatic MVR. This high morbidity rate of open heart surgery has motivated further research into developing a safer and less risky alternative to repair MV. Much of the research involves use of cardiac catheterization. Recently, the inventor of the present invention presented a thesis regarding "mitral valve cerclage coronary sinus annuloplasty (MVA" showing outstanding results of MVR treatment through applying circular pressure around the mitral annulus (MA). This thesis has been filed through PCT as an international patent application (PCT application number PCT/US2007/023836) and has been published (International publication number WO2008/060553).

The aforementioned thesis and published patent application disclosed the mitral cerclage coronary annuloplasty (MVA) procedure. Briefly explained, a catheter is placed in coronary sinus after accessing the right atrium through the jugular vein, and then a cerclage suture is passed through the proximal septal vein. This cerclage suture can easily pass through right ventricular outflow tract (RVOT), and this inventor defines this technique as "simple mitral cerclage annuloplasty". Then, the cerclage suture can be easily pulled into the right atrium thus placing the cerclage suture circumferentially around the mitral annulus. Once positioned, tension is applied to the cerclage suture, thereby tightening the mitral valve. This brings together the two lobes of the MV so that they are approximated and reduce the size of its incomplete closure. This procedure can theoretically obtain very similar results to those that conventional surgeries can obtain by directly tightening the mitral annulus, and shows an immediate reduction of MVR.

However, the cerclage suture passes through the tricuspid valve and the heart, so it may reduce the function of the valve or may damage the valve and other parts. The inventor has developed a tissue protection device for the coronary sinus and the tricuspid valve and has filed a patent application as a technology for protecting tissues in a body (heart) and it has been registered (Korean Patent No. 10-1116867, registered on Feb. 8, 2012).

DISCLOSURE

Technical Problem

The present invention is proposed to improve the technology disclosed in Korean Patent No. 10-1116867 of the inventor and provides a tissue protection device for mitral valve cerclage annuloplasty, whereby the device can protect tissues in the body from a cerclage suture having a simpler structure than the suture used in cerclage annuloplasty.

Technical Solution

In order to achieve the object of the present invention, a tissue protection device for mitral valve cerclage annuloplasty of the present invention is a hollow cylindrical tube where cerclage sutures 10a and 10b are inserted, in which a hole 22 is formed at a predetermined portion of the cylindrical tube so that a coronary sinus cerclage suture 10a inserted in a coronary sinus comes out of the cylindrical tube, and a lower section from the hole is inserted into a tricuspid valve to protect tissues of the tricuspid valve and a ventricular septum.

The cylindrical tube may have: a stem section 23 at an upper portion; a support section 26 connected to the stem section, having the hole, defined at a predetermined portion over and under the hole, and being more rigid than a tricuspid valve insert; and a tricuspid valve insert 24 connected to the support section and protecting tissues of the tricuspid valve and the ventricular septum. The tube may be thicker at the support section than at the tricuspid valve insert.

A protrusion 27 may be formed at a predetermined portion of the cylindrical tube to inform a user of the position of the coronary sinus.

The coronary sinus cerclage suture 10a and the tricuspid valve cerclage suture 10b may be connected to each other, and the coronary sinus cerclage suture 10*a* may be formed to be more rigid than the tricuspid valve cerclage suture 10*b*.

A stopper 24*a* preventing the cylindrical tube from going deep inside the myocardium may be formed at a lower end portion of the cylindrical tube, and the stopper 24*a* may be a circular protrusion.

The device may become narrower as it goes to an end to cover a cerclage suture in the ventricular septum.

Advantageous Effects

As described above, the tissue protection device for mitral valve cerclage annuloplasty of the present invention has a simple structure for protecting the body in mitral valve cerclage annuloplasty performed on a patient with mitral regurgitation, so it is possible to provide convenience and safety in annuloplasty.

BEST MODE

Hereinafter, the tissue protection device for mitral valve cerclage annuloplasty of the present invention will be described in detail with reference to the accompanying drawings.

Figure 1:
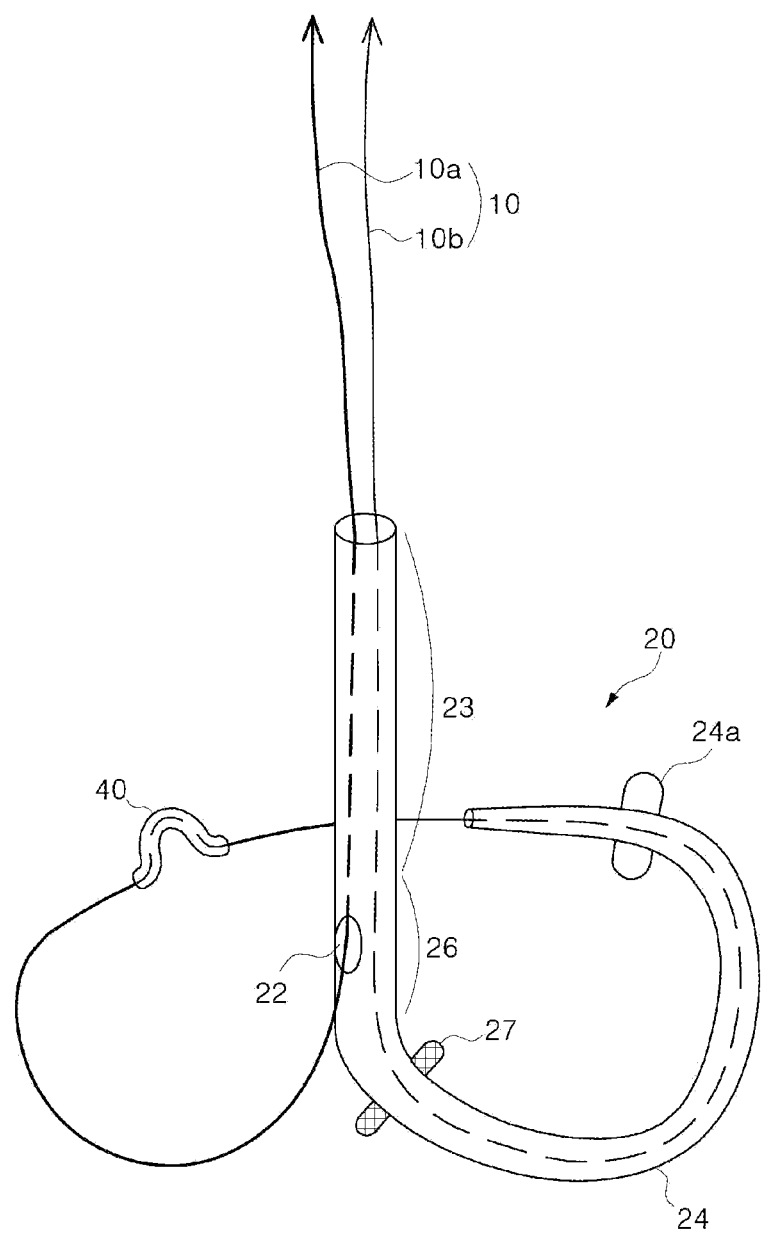
FIG. 1 is a schematic perspective view of the tissue protection device for mitral valve cerclage annuloplasty according to an embodiment of the present invention.
Figure 2:
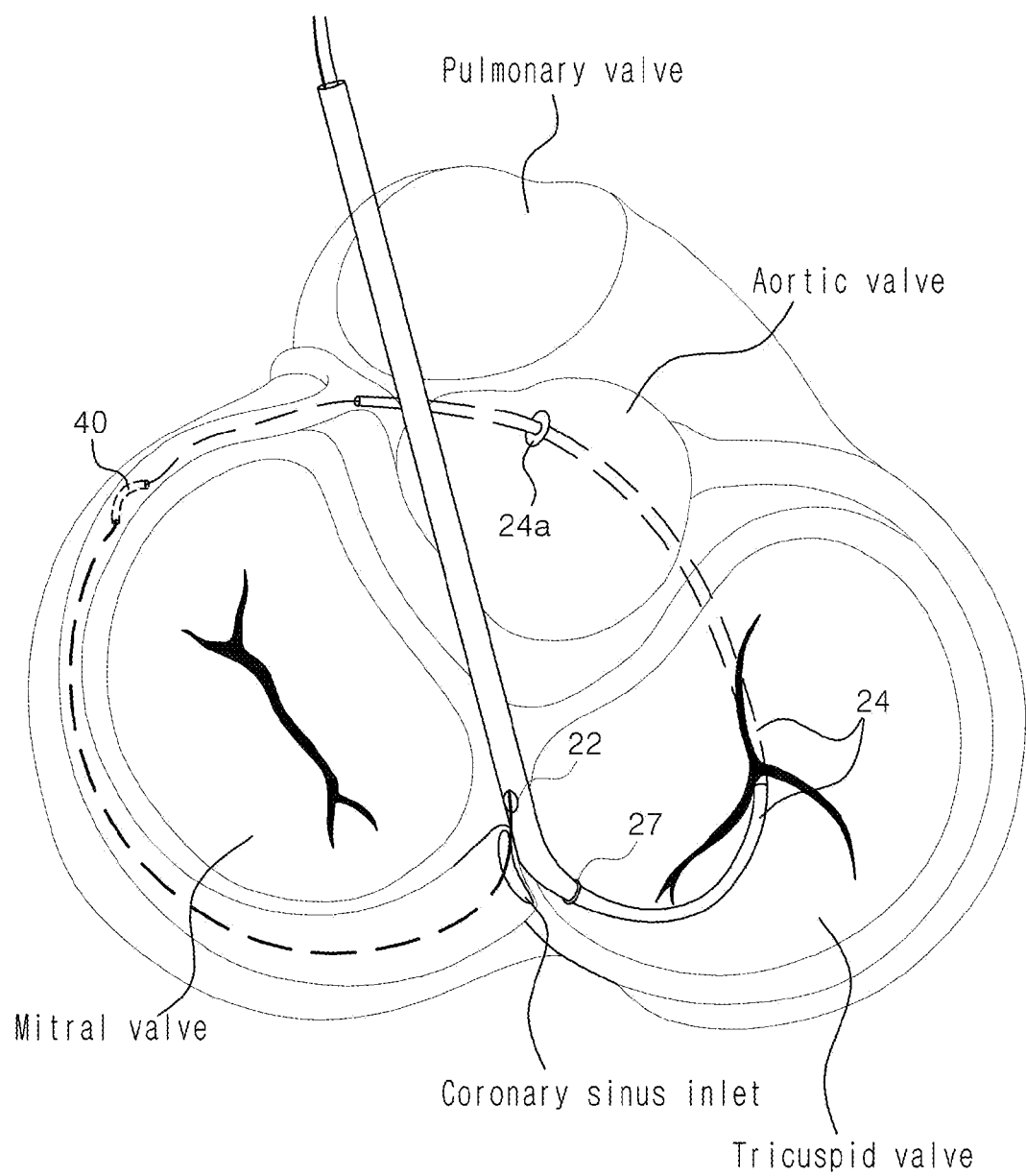
FIG. 2 is a virtual partial cut view of a heart with the tissue protection device for mitral valve cerclage annuloplasty according to an embodiment of the present invention.

FIG. 1 is a schematic perspective view of the tissue protection device for mitral valve cerclage annuloplasty according to an embodiment of the present invention and FIG. 2 is a virtual partial cut view of a heart with the tissue protection device for mitral valve cerclage annuloplasty according to an embodiment of the present invention.

A cerclage suture 10, which is a very thin thread having a thickness of about 0.014" and used for mitral cerclage coronary sinus annuloplasty (MVA), was named in the meaning that a piece of string comes out of a body after going around a coronary sinus (CS), a tricuspid valve (TV), and a ventricular septum, and when the cerclage suture comes out of a body, it is divided into two pieces at one end and the other end. That is, a cerclage suture is divided into a coronary sinus cerclage suture 10*a* and a tricuspid valve cerclage suture 10*b* in FIG. 1, but it is one continuous string making a circle, as shown in the figure. The cerclage suture may be a string made of synthetic resin such as nylon or a metallic wire (stainless steel or metal coated with nylon). Further, a wire formed by twisting a plurality of thin wires may be used. When the cerclage suture 10 is made by twisting a plurality of strings (wires), it is also called a "cerclage rope" or a "cerclage wire" and it is also a kind of cerclage suture.

A tissue protection device 20 is a hollow cylindrical tube where the cerclage sutures 10*a* and 10*b* are inserted. The tissue protection device 20 is a hollow cylindrical tube, that is, it has an empty inside and is manufactured as thick as a 4Fr catheter. The material is a soft and flexible rubber or synthetic resin. Alternatively, a metal spring coated with biological synthetic resin may be used.

As for each part of the tissue protection device 20, the device is composed of a stem section 23 that is the upper part, a support section 26 that is the middle part, and a tricuspid valve insert 24 that is the lower part. The parts collectively make one hollow thin cylindrical tube.

The tissue protection device of the present invention has a hole 22 at a predetermined position and the hole 22 is a part through which the coronary sinus cerclage suture 10*a* inserted in a coronary sinus comes out of the cylindrical tube. The support section 26 is defined to predetermined positions over and under the hole 22, the step section 23 is defined over the support section, and the tricuspid valve insert 24 for protecting a tricuspid valve and a ventricular septum is defined under the support section.

The coronary sinus cerclage suture 10*a* and the tricuspid valve cerclage suture 10*b* are connected to each other. The cerclage suture 10*a* that is supposed to be inserted into a coronary sinus is not covered with the tube in the coronary sinus, so it may be formed to be more rigid than the tricuspid valve cerclage suture 10*b* in order to protect the coronary sinus tissues. The coronary sinus cerclage suture 10*a* is formed thicker than the tricuspid valve cerclage suture 10*b* and thus damage to the coronary sinus tissues due to the coronary sinus cerclage suture is prevented.

The support section 26 where the hole 22 for the coronary sinus cerclage suture 10*a* to come out of the tissue protection device 20 is connected to the stem section 23 and positioned under the stem section 23.

The support section 26 is formed to be more rigid than the stem section 23 or the tricuspid valve insert 24. This is for more stably supporting the coronary sinus cerclage suture 10*a* when the coronary sinus cerclage suture 10*a* comes out of the hole.

Figure 3:
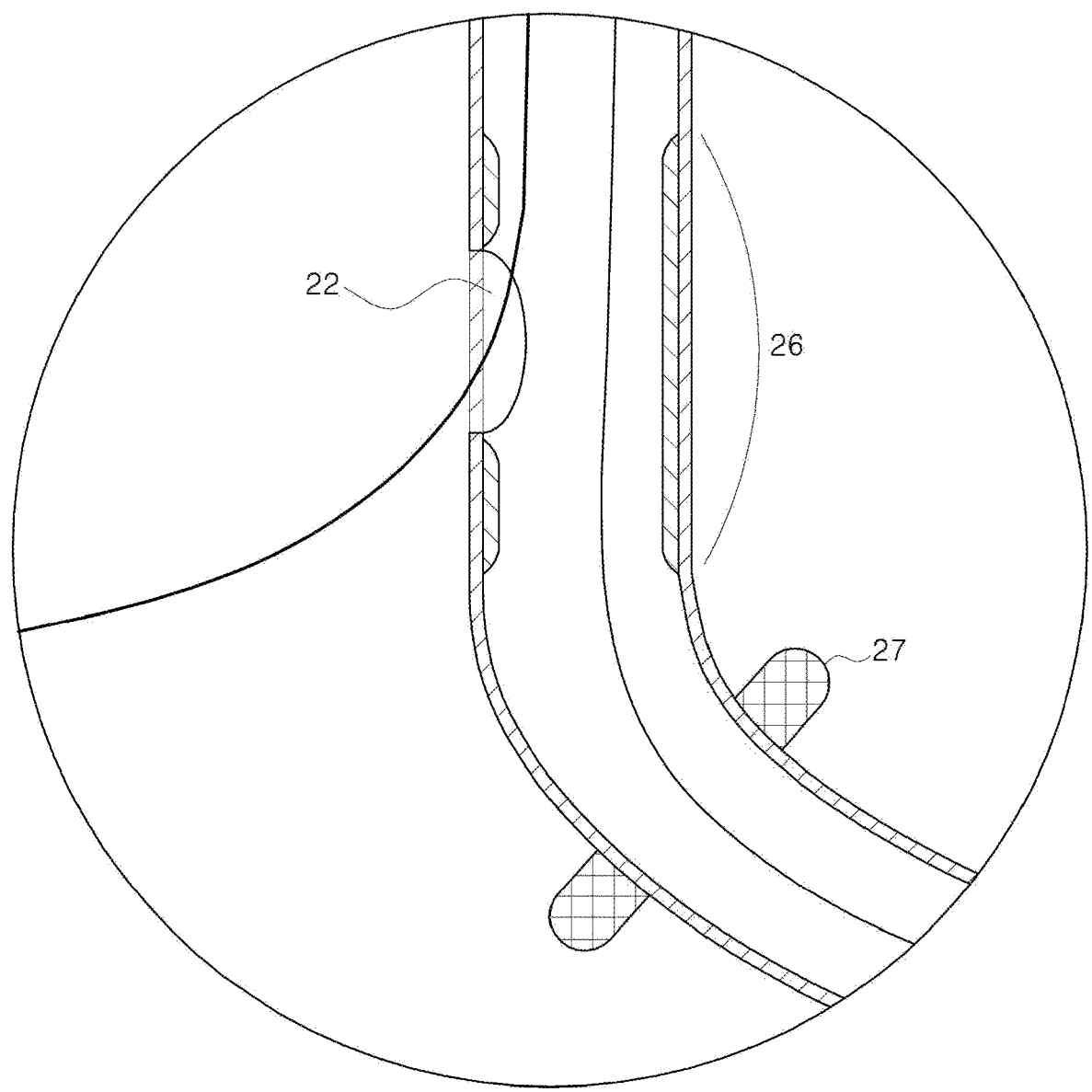
FIG. 3 is a partial cross-sectional view of the tissue protection device for mitral valve cerclage annuloplasty according to an embodiment of the present invention.

FIG. 3 is a partial cross-sectional view of a tissue protection device for mitral valve cerclage annuloplasty according to an embodiment of the present invention.

As shown in FIG. 3, the support section 26 is thicker than the tricuspid valve insert 24. That is, since it is preferable that the support section 26 is more rigid than the tricuspid valve insert 24, the tube is formed thicker at the support section 26 than at the tricuspid valve insert 24. In order to make the support section rigid, the outer diameter of the support section may be increased or the support section may be made of a different material.

The tricuspid valve insert 24 connected to the support section 26 is a part that protects the tricuspid valve and the ventricular septum from the cerclage suture 10*b* that is inserted in the tricuspid valve.

A stopper 24*a* is formed at a lower end portion of the cylindrical tube (that is, a lower end portion of the tricuspid valve insert) to prevent the tissue protection device from going deep inside the myocardium. The stopper 24*a* may be a circular protrusion, as shown in the figure. Further, as shown in the figure, the lower end portion of the cylindrical tube (that is, the lower end portion of the tricuspid valve insert) may become narrower as it goes to the end in order to cover the cerclage suture 10*b* in a ventricular septum.

The distance between an RVOT stopper 24*a* and the hole 22*a* is selected in advance such that the tricuspid valve insert 24 is around two times longer than the distance between an RVOT exit and the coronary sinus hole that is measured from a scanning image of a patient obtained in advance. That is, the distance between the hole 22 and the stopper 24*a* is designed around two times longer than the distance from the stopper to the end. To this end, it may be possible to change the position of the stopper at the tricuspid valve insert 24, but various tissue protection devices having different distances between the hole 22 and the stopper 24a may be provided.

When the coronary sinus cerclage suture 10a coming out of the tissue protection device 20 is inserted into the coronary sinus, the hole 22 is locked to the edge of a CS inlet. Accordingly, the stopper 24a of the tricuspid valve insert 24 (RVOT exit stopper) and the hole 22 are fixed, so the tricuspid valve insert 24 is curved into a reverse C-shape as long as the length without being in contact with the wall of the tricuspid valve (TV). Accordingly, erosion of the tricuspid valve due to the cerclage suture 10 is prevented and movement of lobes of the mitral valve is less limited.

On the other hand, a protrusion 27 may be formed on the outer side of the tissue protection device 20, as shown in the figure. The protrusion 27 prevents the tissue protection device from being excessively inserting into the body by locking to a tissue inside the body and supports a side when the tricuspid valve insert 24 is curved in a reverse C-shape.

The embodiments described above are just examples of the present invention and the scope of the present invention is not limited to the embodiments. The present invention may be changed, replaced, and modified in various ways by those skilled in the art without departing from the scope of the present invention described in claims.

INDUSTRIAL APPLICABILITY

The present invention can be used for a tissue protection device for mitral valve cerclage annuloplasty and, more particularly to a tissue protection device for protecting tissues of the body (heart) during mitral valve cerclage annuloplasty that is performed on a mitral valve cerclage patient with mitral regurgitation.

The invention claimed is:

1. A cerclage assembly for mitral valve annuloplasty, comprising:
    a hollow tube having an upper open end, a lower open end, and a side hole on a side of the tube, wherein the hollow tube has a C-shaped section located between the side hole and the lower open end;
    a cerclage suture having a proximal segment and a distal segment, wherein the cerclage suture travels through and around the tube in the following loop path:
    into the upper open end of the tube;
    through the tube towards the lower open end;
    out the lower open end of the tube;
    forming a loop outside the tube;
    into the side hole of the tube;
    through the tube towards the upper open end;
    out the upper open end of the tube;
    wherein both the proximal segment and the distal segment of the cerclage suture travel into or out of the upper open end;
    wherein both the proximal segment and distal segment of the cerclage suture are positioned outside the tube.

2. The cerclage assembly of claim 1, wherein the side hole is permanently open.

3. The cerclage assembly of claim 1, further comprising a stopper on the hollow tube located between the side hole and the lower open end.

4. The cerclage assembly of claim 3, further comprising a protrusion on the hollow tube located between the stopper and the side hole.

5. The cerclage assembly of claim 3, wherein the distance between the side hole of the tube and the stopper is about twice the distance from the stopper to the lower open end of the tube.

6. The cerclage assembly of claim 1, wherein a support section of the hollow tube spans the side hole, and wherein the hollow tube is thicker at the support section than the C-shaped section.

7. The cerclage assembly of claim 1, wherein a support section of the hollow tube spans the side hole, and wherein the support section is more rigid than the C-shaped section.

8. A method for assembling a cerclage assembly for mitral valve annuloplasty, comprising:
    having a hollow tube with an upper open end, a lower open end, and a side hole on a side of the tube;
    having a cerclage suture with a proximal segment and a distal segment;
    inserting the cerclage suture into the upper open end of the tube;
    advancing the cerclage suture through the tube towards the lower open end;
    advancing the cerclage suture out the lower open end of the tube;
    looping the cerclage suture outside the tube;
    inserting the cerclage suture into the side hole of the tube;
    advancing the cerclage suture through the tube towards the upper open end;
    advancing the cerclage suture out the upper open end of the tube;
    wherein both the proximal segment and distal segment of the cerclage suture are positioned outside the tube.

9. The method of claim 8, wherein the side hole is permanently open.

10. The method of claim 8, forming a C-shape curve at a section of the hollow tube located between the side hole and the lower open end.

11. The method of claim 8, further comprising connecting the proximal segment and distal segment of the cerclage suture together.

* * * * *